US006322966B1

US 6,322,966 B1

(12) United States Patent
Zhong et al.

(10) Patent No.: US 6,322,966 B1
(45) Date of Patent: Nov. 27, 2001

(54) VIRAL SPECIFIC REQUIREMENTS FOR SELF-PRIMING RNA REPLICATION OF HEPATITIS C VIRUS REPLICASE

(76) Inventors: Weidong Zhong, 40 Elmar Cir., Royersford, PA (US) 19468; Zhi Hong, 100 Briar Rd., Nanuet, NY (US) 10954; Johnson Y. N. Lau, 17 Mattben Dr., Warren, NJ (US) 07059

( * ) Notice: Subject to any disclaimer, the term of this patent is extended or adjusted under 35 U.S.C. 154(b) by 0 days.

(21) Appl. No.: 09/309,670

(22) Filed: May 11, 1999

(51) Int. Cl.[7] ....................................................... C12Q 1/70

(52) U.S. Cl. ........................................... 435/5; 435/235.1

(58) Field of Search ...................................... 435/5, 235.1

(56) References Cited

PUBLICATIONS

Al et al., Expression of recobinant hepatitis C virus non-–structural protein 5B in *Escherichia coli*, Virus Research, vol. 53(2), p. 141–49, Feb. 1998.*

* cited by examiner

*Primary Examiner*—Scott W. Houtteman

(57) ABSTRACT

The present invention relates to identification of the features of an RNA template that provide for efficient "copy-back" self-priming activity of hepatitis C virus replicase. This activity can be used to screen for anti-HCV replicase compounds, or to characterize the biological relevance of lead compounds that have already been identified. The specific features of the optimal RNA templates can be used for developing a system to characterize HCV NS5B polymerase mechanistically and kinetically, and for designing small RNA molecules to co-crystallize with HCV NS5B polymerase.

17 Claims, 2 Drawing Sheets

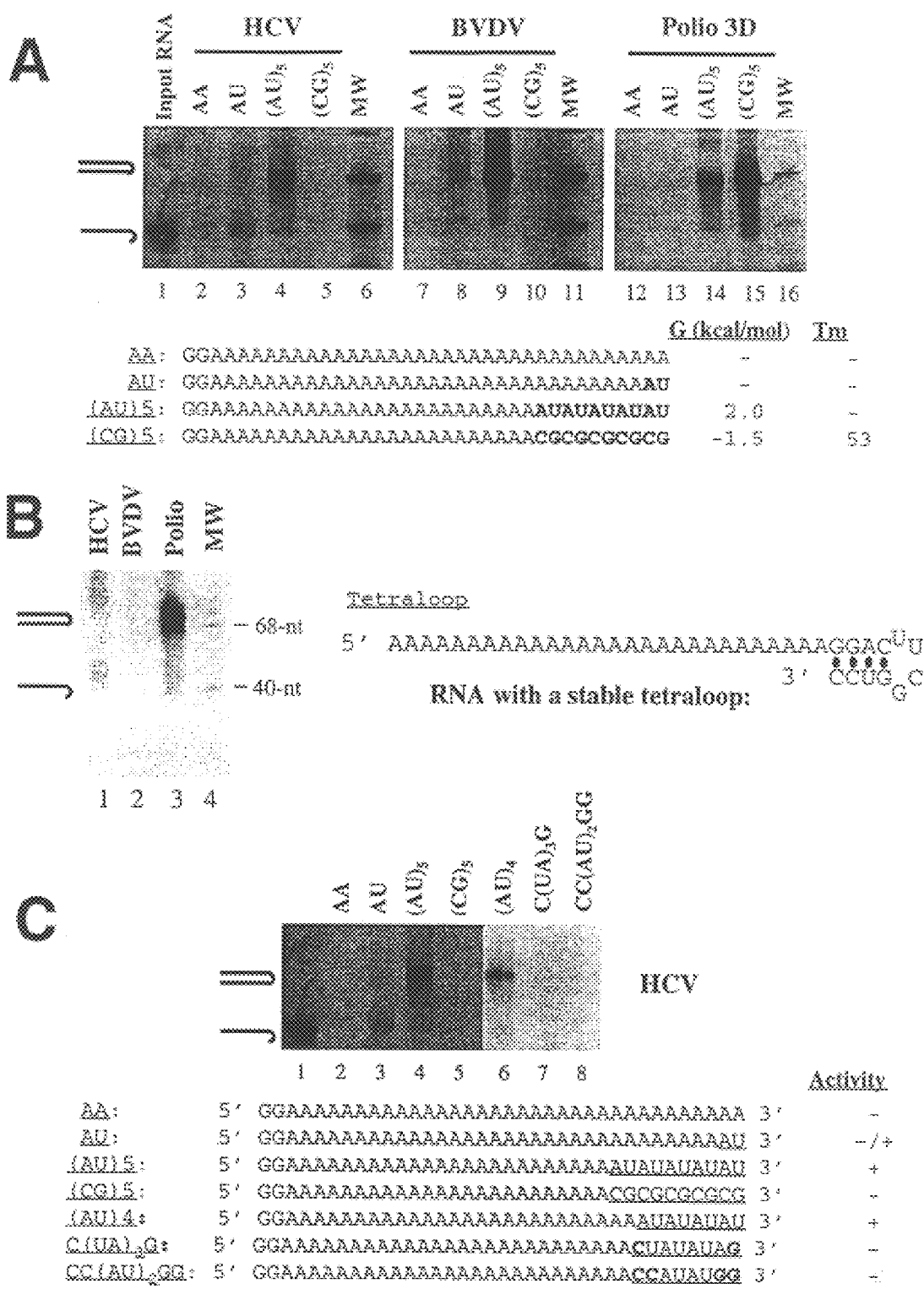

Fig. 2 Minimal Length Requirements for the 3' Stemloop by Different Viruses
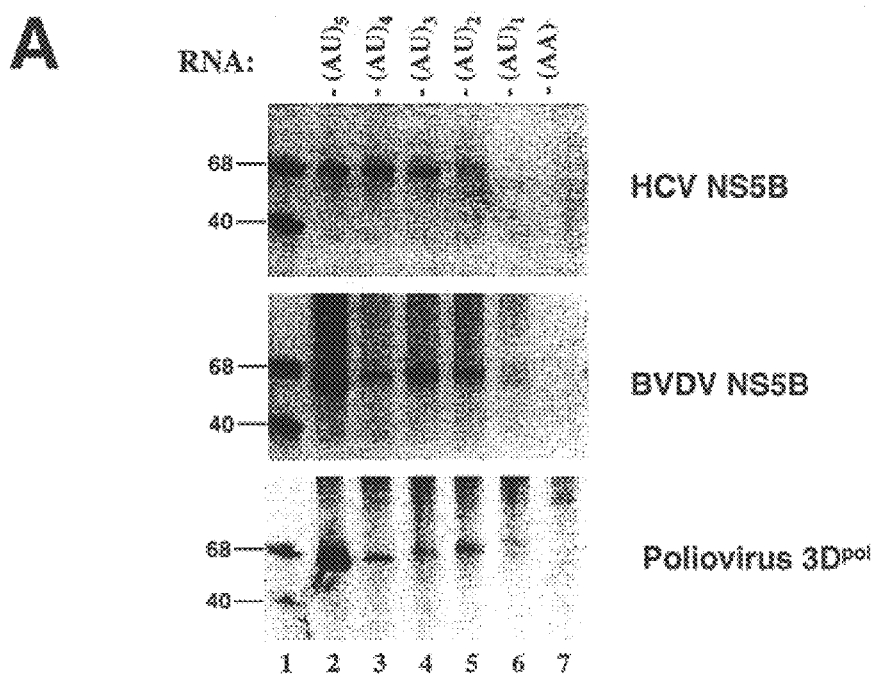
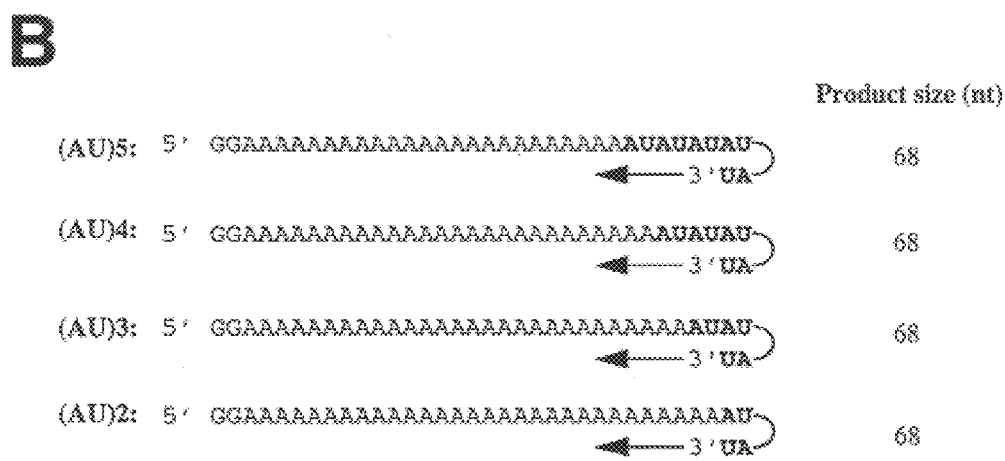

VIRAL SPECIFIC REQUIREMENTS FOR SELF-PRIMING RNA REPLICATION OF HEPATITIS C VIRUS REPLICASE

FIELD OF THE INVENTION

The present invention relates to identification of optimal properties of an RNA template for "copy-back" self-priming RNA synthesis of hepatitis C virus replicase. This activity can be used to screen for anti-HCV replicase compounds, or to characterize the biological relevance of lead compounds that have already been identified.

BACKGROUND OF THE INVENTION

Infection by hepatitis C virus (HCV) is a compelling human medical problem. HCV is recognized as the causative agent for most cases of non-A and non-B hepatitis, with an estimated prevalence of 170 million cases (i.e., 2–3%) globally [Choo, et al., Science, 244: 359–362 (1989); Kuo, et al., Science, 244: 362–364 (1989); Purcell, FEMS Microbiology Reviews, 14: 181–192 (1994); Van der Poel, C. L., Current Studies in Hematology and Blood Transfusion, H. W. Reesink, Ed., (Basel: Karger), pp. 137–163 (1994)]. Four million individuals may be infected in the United States alone [Alter, and Mast, Gastroenterol. Clin. North Am., 23: 437–455 (1994)].

Upon first exposure to HCV only about 10% or less of infected individuals develop acute clinical hepatitis, while others appear to resolve the infection spontaneously. In the most instances, however, the virus establishes a chronic infection that persists for decades [Iwarson, FEMS Microbiology Reviews, 14: 201–204 (1994)]. This usually results in recurrent and progressively worsening liver inflammation, which often leads to more severe disease states such as cirrhosis and hepatocellular carcinoma [Kew, FEM Microbiology Reviews, 14: 211–220 (1994); Saito, et al., Proc. Natl. Acad. Sci. USA 87:6547–6549 (1990)]. Currently, there are no broadly effective treatments for the debilitating progression of chronic HCV.

HCV is an enveloped positive-stranded RNA virus belonging to the Flaviviridae family. The HCV genome encodes a polyprotein of 3010–3033 amino acids [Choo, et al. Proc. Natl. Acad. Sci. USA, 88: 2451–2455 (1991); Kato, et al., Proc. Natl. Acad. Sci. USA, 87: 9524–9528 (1990); Takamizawa, et al., J. Virol., 65: 1105–113 (1991)]. The HCV nonstructural (NS) proteins provide catalytic machinery for viral replication. The NS proteins are derived by proteolytic cleavage of the polyprotein [Bartenschlager, et al., J. Virol., 67: 3835–3844 (1993); Grakoui, et al. J. Virol, 67: 2832–2843 (1993); Grakoui, et al., J. Virol., 67: 1385–1395 (1993); Tomei, et al., J. Virol., 67: 4017–4026 (1993)].

Current therapies with alpha interferon alone and the combination of alpha interferon-ribavirin have been shown to be effective in a portion of patients with chronic HCV infection [Marcellin et al., Ann. Intern. Med. 127:875–881 (1997); Reichard et al., Lancet 351:83–87 (1998)]. Vaccine development has been hampered by the high degree of immune evasion and the lack of protection against reinfection, even with the same inoculum [Farci et al., Science 258: 135–140 (1992); Kao et al., J. Med. Virol. 50:303–308 (1996); Shimizu et al., J. Virol. 68:1494–1500 (1994); Wyatt et al., J. Virol. 72:1725–1730 (1998)]. Development of small molecule inhibitors directed against specific viral targets has thus become the focus of anti-HCV research. The determination of crystal structures for NS3 protease [Kim et al., Cell 87:343–355 (1996); Love et al., Cell 87:331–342 (1996); Yan et al., Protein Sci. 7:837–847 (1998)] and NS3 RNA helicase [Yao et al., Nat. Struct. Biol. 4:463–467 (1997)] has provided important structural insights for rational design of specific inhibitors.

One key enzyme encoded by HCV is NS5B, which has been shown to be an RNA-dependent RNA polymerase (RdRp) [Al et al., Virus Res. 53: 141–149 (1998); Behreus et al., EMBO J. 15:12–22 (1996); DeFrancesco et al., Methods Enzymol. 275:58–67 (1996); Lohmann et al., J. Virol 71:8416–8428 (1997); Yuan et al., 1997, Biochem. Biophys. Res. Commun. 232:231–235 (1997); Ferrari et al., J. Virol. 73:1649–54 (1999)]. NS5B is thus believed to be responsible for HCV genome replication. Cellular localization studies revealed that NS5B is membrane associated and distributed in the perinuclear region [Hwang et al., Annu. Rev. Biochem. 63:777–822 (1997)]. This coincides with the distribution of NS5A [Tanji et al., J. Virol. 69:1575–1581 (1995)], suggesting that NS5A and NS5B may stay together after proteolytic cleavage at the NS5A/NS5B junction. It has been postulated that the nonstructural proteins of HCV (NS3 to NS5B) may assemble into membrane-associated replication complexes that are competent for authentic RNA genome replication.

By itself, HCV NS5B RdRp appears to lack specificity for HCV RNA and can "copy back" heterologous nonviral RNA. This lack of specificity for HCV RNA may reflect the notion that additional viral or cellular factors are required for specific recognition of the replication signal, most likely present at the 3' untranslated region.

The ability of recombinant HCV NS5B to initiate RNA synthesis by a primer-independent mechanism has recently been observed [U.S. patent application Ser. No. 09/305,185 filed May 4, 1999, entitled "De Novo Priming Activity of Hepatitis C Virus Replicase,". De novo priming was also observed with bovine viral diarrhea virus [Kao et al., Virology, 23, pp. 1–7(1999)]. De novo initiation of RNA synthesis is likely to be the mode of initiation of HCV replication in an infected cell.

Although de novo priming/initiation is likely to be the mode of RNA replication employed by HCV, the recombinant polymerase alone can replicate the entire HCV RNA genome initiated from an intramolecular 3' stemloop (via a copy-back primer), resulting in a near dimer-size RNA product (Lohmann et al., J. Virol. 71:8416–28 (1997); Lohmann et al., Virol. 249:108–118 (1998)].

Thus, there is a need in the art to resolve the current uncertainty concerning HCV genome replication.

There is a further need in the art to develop effective therapeutic strategies to inhibit viral specific features of HCV replicase.

The present invention addresses these and other needs in the art.

SUMMARY OF THE INVENTION

The present invention advantageously establishes the RNA template characteristics that optimize the elongative RNA synthesis of hepatitis C virus (HCV) replicase via a copy-back mechanism. The features that have been identified can be harnessed for various primary, and especially secondary, screening assays for anti-HCV compounds. In particular, the present invention permits one to determine whether an HCV NS5B binding compound or inhibitor is capable of selectively blocking HCV NS5B replicase activity, without adversely affecting host cell replication and transcription processes.

Thus, in one embodiment, the invention provides an assay system for hepatitis C virus (HCV) replicase activity. The assay system comprises an RNA template that has an unstable, small stemloop at the 3' end and is capable of supporting copy-back RNA synthesis. Also provided in the assay system are an enzymatically active amount of HCV non-structural protein 5B (NS5B), ATP, GTP, CTP, and UTP nucleoside triphosphates (NTPs), wherein one of the NTPs is radiolabeled, and an assay buffer that supports replication activity of NS5B.

The invention also provides a method for detecting hepatitis C virus (HCV) replicase activity. This method measures the nucleic acid synthesized by an HCV non-structural protein 5B (NS5B) on an RNA template that has an unstable, small stemloop at the 3' end and is capable of forming a copy-back structure in the presence of ATP, GTP, CTP, and UTP nucleoside triphosphates (NTPs), wherein one of the NTPs is radiolabeled, and an assay buffer that supports replication activity of NS5B.

Thus, one object of the invention is to provide an assay system for characterizing the HCV replicase activity via copy-back mechanism.

Another object of the invention is to provide a method for mechanistic and kinetic analysis of HCV replicase.

Another object of the invention is to provide characteristics of an RNA template that can be used for designing small RNA molecules for co-crystallization studies with HCV replicase protein.

These and other objects of the invention have been achieved, as described in further detail in the accompanying drawings and the following Detailed Description of the Invention.

BRIEF DESCRIPTION OF THE DRAWINGS

FIGS. 1A–1C show viral specific requirements of the 3' primer for copy-back RNA synthesis by HCV, BVDV and polivirus replicase proteins. RNA templates with different sequences at the 3' terminus were tested. The templates used are "AA", "AU", "(AU)$_5$", "(CG)$_5$", "tetraloop", "(AU)$_4$", "C(UA)$_3$G" and "CC(AU)$_2$GG" (SEQ ID NO: 1,2,3,4,5,6,7 and 8, respectively). The positions of the input templates and the elongated dimer-size products are indicated. The results show that only "(AU)$_5$" and "(AU)$_4$" templates produced dimer-size products for HCV NS5B (Lane 4 in A; lanes 4 and 6 in C). Introduction of G:C basepairs into the 3' stemloop region is detrimental to the activity of HCV NS5B (Lane 5 in A; lane 1 in B; and lanes 5, 7, 8 in C). Lack of basepairing capability at the 3' terminus also eliminates product formation (Lanes 2 and 3 in A). In contrast, poliovirus 3D$^{pol}$ RdRp prefers RNAs with stable stemloops at the 3' terminus for activity (Lanes 14, 15 in A; and lane 3 in B). BVDV NS5B (a closely related virus to HCV) has similar template requirements as HCV NS5B (lanes 7–10 in A; lane 2 in B).

FIGS. 2A–B show the minimal length requirements for the 3' stemloop primer by HCV, BVDV and polivirus polymerase proteins. RNA templates tested contain various copies of alternating A and U bases at the 3' terminus. These RNAs are "(AU)$_5$", "(AU)$_4$", "(AU)$_3$", "(AU)$_2$", "(AU)$_1$" "AA" (SEQ ID NO: 3, 6, 9, 10, 2 and 1, respectively). The copy-back primer structure for HCV NS5B is proposed in (B) based on the uniform size of the products generated by HCV NS5B. A minimum of two copies of alternating A and U bases is required for the HCV NS5B activity, with three to five copies producing higher activity.

DETAILED DESCRIPTION OF THE INVENTION

The invention is based, in part, on the discovery of the features of an RNA template that enhances HCV NS5B protein replication via a "copy-back" mechanism. To further characterize the 3' stemloop required for this elongative RNA synthesis, a number of small synthetic RNAs were designed and tested for their abilities to direct RNA synthesis by HCV RNA polymerase. Surprisingly, small viral RNAs derived from the 3' terminal sequences of both (+)-stranded and (−)-stranded genomes were not very efficient in supporting RNA synthesis, suggesting that the highly stable stemloop structures found at the 3' ends of the RNA genomes may not be preferred in vitro by the viral polymerase. Indeed, several artificially designed synthetic RNAs with 5 G:C pairs or a stable tetraloop at the 3' ends were shown to be poor substrates of HCV and BVDV (a related pestivirus) polymerase.

As noted above, RNA templates with 3' stemloops of different stem stabilities and loop sizes were tested to identify an optimal RNA template to direct copy-back RNA synthesis. This study revealed that an RNA template optimal for RNA replication by HCV NS5B polymerase should have at least the two following features.

(1) An unstable stemloop with weak base-pairing in the stem region. HCV NS5B prefers a template with a weak stemloop at the 3' end, such as A-U pairs over G-C pairs. Although at room temperature the terminal A-U pairs can not form stable stemloop in solution, such weak stemloop can be induced upon binding to the NS5B polymerase. Stable stemloops (such as a stable tetraloop) were inefficient in supporting RNA synthesis in a gel-based RdRp assay. Introduction of one or two G-C basepairs (increasing in the stability of the 3' stemloop) in the stem region was found to be detrimental to the RdRp activity of HCV NS5B. This finding is in contrast to the requirement by the poliovirus 3D$^{pol}$ RdRp, which prefers a stable stemloop. Interestingly, NS5B of BVDV (a closely related virus to HCV) was also found to prefer a less stable stemloop with A-U pairs and can not initiate RNA synthesis efficiently from a G-C pairing primer.

(2) A small stemloop at the 3' end. Several synthetic RNAs with 1 to 5 A-U pairs were designed to investigate the minimal size of the stemloop for most efficient RNA synthesis. The results demonstrated that HCV NS5B was able to initiate RNA synthesis with a minimum 2 A-U pairs, and preferred 3 A-U pairs or more at the 3' end. Thus, adding additional A-U pairs did not seem to affect the RNA synthesis significantly. Interestingly, the RNA products from these RNAs with different A-U pairs appeared to be of the same size. This further supports the notion that only the last four or six bases at the 3' terminus are required to form a small and constant stemloop (most likely induced to fit the active site of NSB polymerase), even when additional A-U pairs are present to form a larger and more stable stemloop.

NS5B of BVDV seemed to require a larger stemloop with 5 A-U pairs because the RNA synthesis was reduced significantly on a template with only 4 A-U pairs. Polioviral polymerase also required the largest stemloop to direct RNA replication.

Based on the above results, HCV polymerase appears to recognize a linear 3' terminus of a RNA template free of any secondary structure. This result can be explained by the presence of a small binding pocket for the template RNA in HCV polymerase. Upon binding to the polymerase, the template is induced to form a small and unstable stemloop to initiate the RNA synthesis. An RNA template with a stable stemloop at the 3' end may not fit in the small binding pocket, or alternatively, the polymerase may prefer to "melt" the stemloop and "restructure" the template/primer complex before initiating the RNA replication. Thus a stable stemloop may not be favored energetically for melting and restructuring. Poliovirus polymerase, on the other hand, can accommodate a larger and stable tetraloop and initiate directly from the preformed primer.

Identification of this intrinsic enzymatic property of HCV NS5B establishes the basis for assays to test antiviral compounds specifically targeting elongation activity of replication. This may provide a unique window of opportunity to develop more potent and biologically relevant inhibitors of HCV.

Of further interest is the discovery that HCV NS5B replicase has slightly different requirements for the RNA template than a related replicase, the NS5B protein from BVDV. Both HCV and BVDV replicases required different template properties than the poliovirus 3D$^{pol}$ RdRp. Thus, the present invention advantageiously permits an investigator to probe differences in activity of potential anti-NS5B agents against different viral replicases. Such an analysis can help dissect a mechanism of action of the specific viral replicase inhibitor. Alternatively, highly specific reagents can be developed and tested this way.

General Definitions

As used herein, the term "copy back" refers to a self-priming mechanism for RNA replication by initiation from an intramolecular 3' stemloop.

The term "stemloop" refers to a secondary structure formed by a single stranded nucleic acid, e.g., RNA, when the strand is folded back on itself to form an antiparrallel duplex via complementary base pairing. The region of complementarity, where the base pairing occurs, is termed the stem. The intervening region between the complementary sequences on the nucleic acid, i.e., that lacks a sequence capable of base pairing, forms a loop structure.

As used herein, the term "complementary" refers to a nucleic acid sequence that, when arranged in an anti-parallel fashion with another nucleic acid sequence, forms Watson-Crick base-pairs. In particular, C and G bases pair together, and A and U bases pair together. G:C base pairs, which involve the formation of three hydrogen bonds, are stronger. The greater the number of G:C base pairs in complementary sequences, the higher the melting termperature ($T_m$) which is needed to denature (melt) the duplex region.

As used herein, the term "copy-back or elongative" refers to a primer dependent mechanism for initiating RNA synthesis in a template-dependent fashion. As used herein, the term "de novo" refers to a primer independent mechanism for initiating RNA synthesis in a template-dependent fashion.

The term "assay system" as used herein refers to an experimental arrangement designed to measure NS5B activity. It can be in a high throughput mode, or an individual assay mode, depending on whether it is adapted for screening or for elucidating mechanisms of activity, for example.

An "RNA template" is an oligonucleotide, preferably of ribonucleotides (HCV NS5B does not use a DNA template efficiently), having a sequence that permits replication by NS5B. In a specific embodiment, the RNA template has a sequence similar to the 3' end of the HCV genome.

NS5B as used herein refers to the gene product encoded by a region near the 3' end of the hepatitis C virus genome. It generally corresponds to amino acid residues 2420–3010 of the HCV polyprotein [see, e.g., Behrens et al., EMBO J. 15:12–22 (1997)]. The protein has a molecular weight of 65 kD, and demonstrates both template dependent (RdRp; RNA dependent RNA polymerase) and template independent (TNTase) catalytic addition of ribonucleotides to the 3' termini of exogenous RNA in a $Mg^{2+}$-dependent process [see International Patent Publication WO 96/37619; Lohmann et al., Virology 249:108–118 (1998)]. $Mn^{2+}$ can be substituted for $Mg^{2+}$, and indeed appears to be preferred [Ferrari et al., J. Virol. 73:1649–54 (1999)]. Thus, an assay buffer that supports replication activity (i.e., RNA polymerization or the catalytic addition of ribonucleotides to the 3' termini of exogenous RNA) requires a divalent cation such as $Mg^{2+}$ or, preferably, $Mn^{2+}$. Gliotoxin inhibits HCV NS5B RdRp in a dose dependent manner [Ferrari et al., supra]. The ability of NS5B to polymerize ribonucleotides may be referred to as polymerase or as replicase activity, or as enzymatic activity.

As used herein, the terms "replication" or "replicate", "polymerization" or "polymerize", and "transcription" and "transcribe" may be used interchangably in connection with NS5B to refer to NS5B enzymatic activity.

A nucleoside triphosphate refers to ribonucleotide substrates of the NS5B. A radiolabel on a ribonucleotide triphosphate can be $^{33}$P or $^{32}$P, with the latter providing a stronger signal. Other radioisotopes can also be used, including but not limited to tritium ($^{3}$H) and carbon 14 ($^{14}$C). Other types of labels are likely to interfere unacceptably with enzymatic activity and are therefore not desirable. Labeling of the α-P will result in incorporation of the label with each added NTP onto the elongated product.

In a specific embodiment, the term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term about or approximately depends on the particular system under study, and can be readily appreciated by one of ordinary skill in the art.

Various aspects of the invention are disclosed in greater detail in the following sections related to NS5B, preparation of oligonucleotide templates, and assays. The headings (bold), subheadings (bold, italics), and sections of the application are provided to facilitate understanding of the invention, and are not intended to be limiting.

HCV Replicase (NS5B)

HCV NS5B for use in the assays of the present invention can be obtained from any source, although recombinant production is preferred to ensure an adequate supply of the enzyme for study.

In a preferred embodiment, NS5B is expressed in *E. coli* as a soluble product lacking the hydrophobic C terminus, and particularly the tetraleucine motif responsible for the solubility profile of full-length NS5B [Ferrari et al., J. Virol. 73:1649–54 (1999)].

In this specific embodiment, a consensus NS5B of HCV-1b was cloned from the BK isolate. A computer intensive approach was undertaken to identify the non-consensus mutations in NS5B of the BK isolate. The amino acid sequence of NS5B (BK) was compared to 16 NS5B proteins from different genotypes and subtypes. Four isolates representing genotype 1 subtype a (HCV-1a) and five from HCV-1b were used. The rest were from HCV-2a, 2b, 3a, 3b, 4a, 5a and 6a. Two potential non-consensus mutations were identified: one T at position 329, the other V at position 338 (numbered according to the sequence of unmodified NS5B).

The corresponding amino acids in other isolates were V and A respectively, which are consensus among different genotypes. These mutations were likely introduced into the cDNA clones isolated during reverse transcriptase and polymerase chain reaction (RT-PCR). RT-PCR is a commonly used method to isolate HCV cDNA clones, but this methods lacks a proof-reading process, which is required to prevent misincorporations (or errors) in the cDNA clones. Such mis-incorporations often result in mis-sense mutations at the amino acid level which may lead to functional defects in the protein products of HCV.

To repair these non-consensus mutations, site-directed mutagenesis using the "Quick Change" mutagenesis kit (Stratagene, Calif.) was performed. The resulting clone was verified for correctness by direct sequencing and thus represented the consensus clone of NS5B of the BK isolate. This approach of generating consensus clones has been proven to be essential to obtain biologically validated and functionally correct clones of HCV. This consensus NS5B was subcloned into pET-21b (Novagen) between NheI and BamHI sites. Two codons were engineered at the N-terminus, coding for "MA", replacing the native amino acids (SM) at the N-terminus of NS5B. The C-terminal 21 amino acids were removed to improve the solubility [Ferrari et al., J. Virol. 73:1649–54 (1999)]. A polyhistidine tag (GSHHHHHH) (SEQ ID NO: 11) was engineered to replace the C-terminal domain which facilitates the purification of the enzyme.

Alternatively, a PCR product containing the cDNA region encoding amino acids 2420–3010 of the HCV polyprotein (the NS5B protein) can be cloned into a vector, such as between the BamHI and HindIII sites of the pBlue BacIII vector (Invitrogen), and expressed in Sf9 cells by a baculovirus vector [International Patent Publication WO 96/37619; Behrens et al., EMBO J. 15:12–22 (1996)]. A baculovirus expression system has also been used to express a C-terminally histidine-tagged NS5B construct [Lohmann et al., J. Virol. 71:8416–28 (1997)].

In accordance with the present invention there may be employed conventional molecular biology, microbiology, and recombinant DNA techniques within the skill of the art for the production of NS5B. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis [M. J. Gait ed. (1984)]; Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; A Practical Guide To Molecular Cloning [B. Perbal (1984)]; Current Protocols in Molecular Biology, John Wiley & Sons, Inc. [F. M. Ausubel et al. (eds.) (1994)].

In addition to the preferred consensus NS5B described above, various mutant forms or homologues can be employed. The terms "mutant" and "mutation" mean any detectable change in genetic material, e.g. DNA, or any process, mechanism, or result of such a change. This includes gene mutations, in which the structure (e.g., DNA sequence) of a gene is altered, any gene or DNA arising from any mutation process, and any expression product (e.g., protein) expressed by a modified gene or DNA sequence. The term "variant" may also be used to indicate a modified or altered gene, DNA sequence, enzyme, cell, etc., i.e., any kind of mutant.

"Sequence-conservative variants" of NS5B are those in which a change of one or more nucleotides in a given codon position results in no alteration in the amino acid encoded at that position. "Function-conservative variants" of NS5B are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like).

Synthesis of RNA Oligonucleotide Template

As used herein, the term "oligonucleotide" refers to a nucleic acid, generally of at least 10, preferably at least 15, and more preferably at least 20 nucleotides, preferably no more than 100 nucleotides, that can serve as a template for NS5B, or which is produced as the result of NS5B polymerase activity. The oligonucleotide template of the invention is preferably RNA, since NS5B uses a DNA template poorly.

The present invention advantageously provides an optimized RNA oligonucleotide template for HCV NS5B replication assays. Prior to the present invention, small viral RNAs were found to be inefficient in supporting RNA synthesis. However, by incorporating the features discovered herein in an RNA template, copy-back priming initiated replication can be studied efficiently. This efficiency permits development of various screening assays, as discussed in detail, infra.

An optimized RNA template has an unstable stemloop with weak base-pairing in the stem region, and a small stemloop at the 3' end. The 3' terminus of the RNA template should be linear and free of any secondary structures. Upon binding of HCV polymerase (NS5B), the template should be induced to form a small, unstable stemloop to initiate RNA synthesis. In other words, the unstable, small stemloop can form in the presence of NS5B, which stabalizes the stemloop structure.

An unstable stemloop at the 3' terminus should lack G:C basepairs in the stem region, as these pairs are more stable than A:U pairs. It has been found that the presence of even a single G:C pair in a $C(UA)_3G$ structure significantly decreased replication efficiency. In a specific embodiment, infra, sequences that provide for efficient replicase activity are, in order from most preferred to least preferred, (AU)5 [AUAUAUAUAU (SEQ ID NO: 3)], (AU)4, (AU)3, and (AU)2.

RNA templates for the transcription assays of the invention with a large stemloop at the 3' end may not fit into the binding pocket of NS5B. A template with a stable stemloop, e.g., with a long region of complementarity or one or more G:C basepairs, may not permit the polymerase to "melt" the stemloop and "restructure" the template/primer complex before initiating RNA replication.

Generally, oligonucleotides for use as the template are prepared synthetically, preferably on a nucleic acid synthesizer. RNA template oligonucleotides can also be obtained from commercial sources (Oligos Etc., Inc., Wilsonville, Oreg. Dharmacon Research, Inc., Boulder, Colo.; HHMI Biopolymer/Keck FBRL, Yale University, New Haven, Conn.; Baron Biotech, Milford, Conn.).

Oligonucleotides produced by NS5B replication activity can be labeled, e.g., with $^{32}P$-nucleotides or $^{33}P$-nucleotides. The presence of the label permits detection of nascent oligonucleotides, i.e., distinguishing them from the template. While $^{32}P$ provides a stronger signal, $^{33}P$ is safer to work with.

NS5B Activity Assays

Generally, NS5B polymerase activity assays must be run under conditions that permit polymerization. Generally, this requires the presence of a divalent cation, e.g., $Mg^{2+}$ or $Mn^{2+}$ as disclosed above, sufficient quantities of ribonucleotide triphosphates to serve as substrates for the polymerase, an RNA template as pointed out above, and the NS5B in an isotonically buffered aqueous solution. In a specific embodiment, the assay is performed in an optimal buffer containing 20 mM Hepes, pH7.3, 10 mM $MnCl_2$, 120 mM NaCl, 7.5 mM DTT, 0.25 $\mu$M of RNA template and 0.1 $\mu$M of HCV NS5B protein. The concentration of unlabeled NTPs is 100 $\mu$M, and the concentration of the labeled NTP is 5 $\mu$M of which 0.15 $\mu$M is radiolabeled. Any label can be used. Preferably the label is a phosphorous isotope, e.g., P-33 or P-32.

The reaction can be performed at 30° C., although higher and lower temperatures are possible. For example, other polymerases are more efficient at 37° C. The reaction time can vary, depending on the rate of product formation, but should be long enough to permit at least one complete round of synthesis.

In a preferred embodiment, the reaction can be performed in the presence of candidate inhibitory compounds, e.g., to evaluate the ability of such compounds to inhibit NS5B activity. Such compounds, which may have been identified in a primary screen, e.g., by the ability to bind to NS5B or to inhibit NS5B activity (in a primer-dependent fashion), or which may be identified in a primary screen that takes advantage of efficient copy-back priming on an RNA oligo template, are good lead candidates to develop anti-HCV pharmaceuticals.

As used herein, the term "compound" refers to any molecule or complex of more than one molecule that affects NS5B enzymatic function. The present invention contemplates screens for synthetic small molecule agents, chemical compounds, chemical complexes, and salts thereof as well as screens for natural products, such as plant extracts or materials obtained from fermentation broths.

In these assays, compounds with known replicase inhibitory activity can be used as positive controls. One example of such a compound is gliotoxin, which is a known poliovirus 3D RdRp inhibitor. Other such compounds include nucleotide analogs, such as dideoxy nucleotides, that inhibit synthesis.

High Throughput/Primary Screens

In one embodiment, a copy-back assay system of the invention can be formatted in an automated high throughput screen (HTS) for primary screening of candidate anti-HCV NS5B compounds.

One example of a HTS screen of the invention is scintillation proximity assay (SPA). In such an assay, the RNA template may be biotinylated (e.g. at the 5' end) and the synthesized products are captured onto the streptavidin-coated SPA beads.

Secondary/Mechanism Screens

While the discovery of optimized RNA template features for NS5B replication provides for primary screening assays, particularly in an HTS format, a more important discovery of the invention is to use the HCV replicase activity as a probe for the mechanistic studies of candidate compounds discovered in a primary screen. In particular, the discovery that HCV NS5B requires a linear 3' terminus on the RNA template provides incentive to identify NS5B inhibitory compounds that directly interfere with this process. An advantage of such candidate compounds is that they may be more effective than other types of replication inhibitors, because they target a unique mechanistic step in HCV replication.

The replication assays described infra provide one means to further evaluate NS5B activity. These assays can be readily adapted for dose response or absolute (saturation) inhibition by possible anti-HCV NS5B compounds. For example, an assay system as described infra, comprising 20 mM Hepes, pH7.3, 10 mM $MnCl_2$, 120 mM NaCl, 7.5 mM DTT, 0.25 $\mu$M of RNA template and 0.1 $\mu$M of HCV NS5B protein, 100 $\mu$M of ATP, CTP and GTP, 5 $\mu$M UTP and 0.15 $\mu$M of $\alpha$-$^{33}$P-UTP can be set up in the presence and absence of a dilution series of candidate inhibitory compounds. The ability of such compounds to inhibit replication initiation or elongation can be detected, e.g., by running the reaction for about one hour, extracting the nascent, labeled RNA by phenol/chloroform extraction and ethanol precipitation, separating the nucleic acids on a 15–20% PAGE gel in 8M urea, and detecting products by autoradiography.

Alternatively, a membrane binding assay in which the radiolabeled products are captured to a membrane may be used as the assay format.

EXAMPLES

The invention can be more fully understood by reference to the following examples, which are provided as exemplary of the invention and not limiting of the invention.

EXAMPLE 1

RNA Template Requirements for Replicase Activity

It has been demonstrated by us and others that HCV NS5B RNA-dependent RNA polymerase (RdRp) is capable of directing RNA replication via both primer-dependent (elongative) and primer-independent (de novo) mechanisms. Although de novo priming/initiation is likely to be the mode of RNA replication employed by HCV, the recombinant polymerase alone can replicate the entire HCV RNA genome initiated from an intramolecular 3' stemloop (via the copy-back mechanism), resulting in a near dimer-size RNA product. This Example further characterizes the specific features of the 3' stemloop required for this elongative RNA synthesis. To achieve this, a number of small synthetic RNA templates were designed and tested for their abilities to direct RNA synthesis by HCV RNA polymerase.

Materials and Methods

Templates. Synthetic RNA templates were prepared commercially (Oligos Etc., Inc., Wilsonville, Oreg.). The sequences of the templates are shown in the Figures.

In vitro elongation assay. HCV replicase assay was performed in 20 mM Hepes, pH7.3, 10 mM $MnCl_2$, 120 mM NaCl, 7.5 mM DTT, 0.25 $\mu$M of RNA template and 0.1 $\mu$M of HCV NS5B protein, 100 $\mu$M of ATP, CTP and GTP, 5 $\mu$M of UTP and 0.15 $\mu$M of $\alpha$-$^{33}$P-UTP. BVDV replicase assay was performed in 20 mM Tris.Cl, pH 7.5, 6 mM $MnCl_2$, 0.2 mM $MgCl_2$, 2 mM DTT, 1% CHAPS, 25 mM NaCl, 5% glycerol, 0.25 $\mu$M of RNA template and 0.01 $\mu$M of BVDV NS5B protein, 100 $\mu$M of ATP, CTP and GTP, 5 $\mu$M of UTP, 0.15 $\mu$M of $\alpha$-$^{33}$P-UTP. Poliovirus $3D^{pol}$ replicase assay was performed in 50 mM HEPES, pH 8.2, 3 mM $MgCl_2$, 10 mM DTT, 0.25 $\mu$M of RNA template and 0.05 $\mu$M of $3D^{pol}$ protein, 100 μM of ATP, CTP and GTP, 5 μM of UTP, 0.15 μM of α-$^{33}$P-UTP. The reactions were incubated at 30° C. for 1 hour. Products were extracted with phenol/chloroform, separated on a 15–20% PAGE gel containing 8M urea, and detected by autoradiography.

Source of replicases. The HCV and BVDV NS5B proteins used in these assays are soluble, C-terminally His-tagged forms expressed in *E. coli*, as described in Ferrari et al. [J. Virol. 73:1649–1654 (1999)] and Lai et al. [J. Virol. submitted (1999)], which are specifically incorporated herein by referenced in its entirety. The poliovirus 3D$^{pol}$ protein was obtained in a similar fashion.

Results

Small viral RNAs derived from the 3' terminal sequences of both (+)-stranded and (−)-stranded genomes were not very efficient in supporting RNA synthesis, suggesting that the highly stable stemloop structures found at the 3' ends of the RNA genomes may not be preferred in vitro by the viral polymerase.

Several artificially designed synthetic RNAs with 5 G-C pairs or a stable tetraloop at the 3' ends were shown to be poor substrates of HCV and BVDV (a related pestivirus) polymerase (FIG. 1A, lanes 5 and 10 and 1B, lanes 1 and 2). HCV NS5B prefers a template with a weak stemloop at the 3' end, such as A-U pairs over GC pairs (FIG. 1A, compare lanes 4 and 5). Although at room temperature, the terminal A-U pairs can not form a stable stemloop in solution, such weak stemloop can be induced upon binding to the NS5B polymerase.

Stable stemloops (such as the stable tetraloop) were inefficient in supporting RNA synthesis by HCV NS5B in the gel-based RdRp assay (FIG. 1B, lane 1). Introduction of one or two G:C basepairs (increasing in the stability of the 3' stemloop) in the stem region is detrimental to the RdRp activity of HCV NS5B (FIG. 1C, lanes 7 and 8 vs. lane 6). This finding is in contrast to the requirement by the poliovirus 3Dpol RdRp (FIG. 1A, lane 15; 1B, lane 3), which prefers a stable stemloop. A recent study by others also supports the observation that poliovirus polymerase prefers a primer stably annealed to the template [Arnold and Cameron, J. Biol. Chem. 274:2706–16 (1999)]. Interestingly, NS5B of BVDV (a closely related virus to HCV) also prefers a less stable stemloop with A:U pairs and can not initiate RNA synthesis efficiently from a G:C pairing primer (FIG. 1A, lane 9 vs. lane 10).

Several synthetic RNAs with 1 to 5 A-U pairs were designed to investigate the minimal size of the stemloop required for efficient RNA synthesis. Our results demonstrated that HCV NS5B was able to initiate RNA synthesis with a minimum 2 A-U pairs, and preferred 3 A-U pairs or more at the 3' end, adding additional A-U pairs did not seem to affect the RNA synthesis significantly (FIG. 2A, top panel, lanes 2–5). Interestingly, the RNA products from these RNAs with different A-U pairs appeared to be of the same size (~68-nt) (FIG. 2A, top panel). This further supports the notion that only the last four or six bases at the 3' terminus are required to form a small and constant stemloop (most likely induced to fit the active site of NSB polymerase), even when additional A:U pairs are present to form a larger and more stable stemloop (FIG. 2B).

NS5B of BVDV seemed to require a larger stemloop with 5 A-U pairs at the 3' terminus because the RNA synthesis was reduced significantly on a template with only 4 A-U pairs (FIG. 2A, middle panel, compare lanes 2 and 3). Polioviral polymerase also required the largest stemloop to direct RNA replication (FIG. 2A, bottom panel, lane 2 vs. lanes 3–6).

DISCUSSION

Based on the above results, two features have been identified for optimal copy-back initiation of replication by HCV polymerase: (1) an unstable stemloop with weak base-pairing in the stem region; and (2) a small stemloop at the 3' end. HCV polymerase appears to recognize the linear 3' terminus of a RNA template free of any secondary structures. This may be due to a small binding pocket for the template RNA in HCV polymerase. Upon binding to the polymerase, the template is induced to form a small and unstable stemloop to initiate the RNA synthesis. An RNA template with a stable stemloop at the 3' end may not fit in the small binding pocket, or alternatively, the polymerase may prefer to "melt" the stemloop and "restructure" the template/primer complex before initiating the RNA replication. Thus a stable stemloop may not be favored energetically for melting and restructuring. Poliovirus polymerase, on the other hand, can accommodate a larger and more stable stemloop and initiate directly from the copy-back primer.

The discovery of viral specific requirements for efficient copy-back RNA replication will impact the following areas of research and antiviral drug development:

1) Establishment of efficient gel-based RdRp assays for screen and evaluation of antiviral inhibitors.
2) Development of a system to characterize the NS5B polymerase kinetically and mechanistically.
3) Design of a small RNA for co-crystallization with NS5B polymerase.
4) Investigation of mechanistic inhibitors for mis-incorporation or chain-termination.

Further optimization of such small RNA template based on these findings may lead to an even better substrate for the HCV polymerase. At present, no report of any small synthetic RNA substrates that support the RNA replication is available. Larger enzymatically-produced RNA substrates are less amenable for purposes listed above. Thus, this discovery permits preparation of small RNA templates for evaluating HCV replication mechanisms and screening for replication antagonists.

The present invention is not to be limited in scope by the specific examples disclosed herein. Various embodiments and alternatives are part of this invention, the full scope of which is delineated by the claims appended hereto.

All sizes and molecular weights are provided for the sake of convenience in understanding the invention, and should be regarded as approximate and not limiting thereof.

Patents, patent applications, references, and methods cited in this application are incorporated herein by reference in their entireties.

What is claimed is:

1. An assay system for hepatitis C virus (HCV) replicase activity, which assay system comprises an RNA template that has an unstable, small stemloop at the 3' end and is capable of forming a copy-back structure, an enzymatically active amount of HCV non-structural protein 5B (NS5B), ATP, GTP, CTP, and UTP nucleoside triphosphates (NTPs), wherein one of the NTPs is radiolabeled, and an assay buffer that supports replication activity of NS5B.

2. The assay system of claim 1, wherein the NS5B is a soluble and active NS5B expressed in *Escherichia coli*.

3. The assay system of claim 1, wherein the RNA template contains a sequence selected from the group consisting of (AU)5, (AU)4, (AU)3, and (AU)2 at the 3' terminus.

4. The assay system of claim 1, wherein the RNA template lacks any G:C bases capable of base-pairing to form a stemloop at the 3' terminus.

5. The assay system of claim 1, wherein the label is a radioactive phosphate.

6. The assay system of claim 1, wherein the labeled base is α-$^{33}$P-NTP that hydrogen bonds to a base in the template.

7. The assay system of claim 1, wherein the assay buffer comprises 20 mM Hepes, pH7.3, 10 mM MnCl$_2$, 120 mM NaCl, 7.5 mM DTT, 0.25 μM of RNA template and 0.1 μM of HCV NS5B protein, 100 μM of ATP, CTP and GTP, 5 μM of UTP, 0.15 μM of α-$^{33}$P-UTP, and the assay is performed at 30° C.

8. A method for detecting hepatitis C virus (HCV) replicase activity, which method comprises detecting the presence of a nucleic acid synthesized by an HCV non-structural protein 5B (NS5B) on an RNA template that has an unstable, small stemloop at the 3' end and is capable of forming a copy-back structure in the presence of ATP, GTP, CTP, and UTP nucleoside triphosphates (NTPs), wherein one of the NTPs is radiolabeled, and an assay buffer that supports replication activity of NS5B.

9. The method according to claim 8, wherein detecting the nucleic acid synthesized by NS5B comprises evaluating an autoradiograph of reaction products separated by gel electrophoresis.

10. The method according of claim 8, wherein the NS5B is a soluble NS5B expressed in *Escherichia coli*.

11. The method according to claim 8, wherein the RNA template contains a sequence selected from the group consisting of (AU)5, (AU)4, (AU)3, and (AU)2 at the 3' terminus.

12. The method according to claim 8, wherein the RNA template lacks any G-C bases capable of base-pairing to form a stemloop at the 3' terminus.

13. The method according to claim 8, wherein the label is a radioactive phosphate.

14. The method according to claim 8, wherein the labeled base is a α-$^{33}$P-NTP that hydrogen bonds to a base in the template.

15. The method according to claim 8, wherein the assay buffer comprises 20 mM Hepes, pH7.3, 10 mM MnCl$_2$, 120 mM NaCl, 7.5 mM DTT, 0.25 μM of RNA template and 0.1 μM of HCV NS5B protein, 100 μM of ATP, CTP and GTP, 5 μM of UTP, 0.15 μM of α-$^{33}$P-UTP, and the assay is performed at 30° C.

16. A composition comprising an HCV NS5B protein and an RNA template that has an unstable, small stemloop at the 3' end and is capable of forming a copy-back structure.

17. The composition of claim 16 which is in an assay buffer that supports replication activity of NS5B.

* * * * *